United States Patent
Adrian et al.

(10) Patent No.: US 7,462,277 B2
(45) Date of Patent: Dec. 9, 2008

(54) CONTINUOUS METHOD FOR SEPARATING A $C_4$ CUT

(75) Inventors: Till Adrian, Bobenheim-Roxheim (DE); Thomas Hill, Ludwigshafen (DE); Klaus Kindler, Harthausen (DE); Bernd Heida, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 527 days.

(21) Appl. No.: 10/521,364
(22) PCT Filed: Jul. 22, 2003
(86) PCT No.: PCT/EP03/07991
§ 371 (c)(1), (2), (4) Date: Jan. 14, 2005
(87) PCT Pub. No.: WO2004/011406
PCT Pub. Date: Feb. 5, 2004

(65) Prior Publication Data
US 2006/0021911 A1 Feb. 2, 2006

(30) Foreign Application Priority Data
Jul. 24, 2002 (DE) .............................. 102 33 620

(51) Int. Cl.
*C10G 11/08* (2006.01)
(52) U.S. Cl. .................. 208/115; 585/258; 585/259; 585/324; 585/664; 585/668; 585/671; 585/833; 585/864
(58) Field of Classification Search ............. 208/115; 585/833, 864, 258, 259, 324, 664, 668, 671
See application file for complete search history.

(56) References Cited

U.S. PATENT DOCUMENTS

| | | | |
|---|---|---|---|
| 5,563,299 A * | 10/1996 | Paludetto et al. ............ 568/697 |
| 6,137,023 A | 10/2000 | Dorbon et al. | |
| 2002/0087040 A1 | 7/2002 | Marchionna et al. | |
| 2003/0181772 A1 * | 9/2003 | Meyer et al. ................ 585/324 |

FOREIGN PATENT DOCUMENTS

| | | |
|---|---|---|
| DE | 198 18 810 | 10/1999 |
| DE | 100 22 465 | 11/2001 |
| DE | 101 05 660 | 8/2002 |
| DE | 102 19 375 | 11/2003 |
| EP | 0 667 329 | 8/1995 |

* cited by examiner

*Primary Examiner*—Glenn Caldarola
*Assistant Examiner*—Prem C. Singh
(74) *Attorney, Agent, or Firm*—Oblon, Spivak, McClelland, Maier & Neustadt, P.C.

(57) ABSTRACT

In a continuous process for fractionating a $C_4$ fraction ($C_4$) by extractive distillation using a selective solvent (LM) in an extractive distillation column (EDK), it is proposed that a dividing wall (TW) is installed in the longitudinal direction in the extractive distillation column (EDK) to form a first region (A), a second region (B) and a lower combined column region (C) and a top stream ($C_4H_{10}$) comprising the butanes is taken off from the first region (A), a top stream ($C_4H_8$) comprising the butenes is taken off from the second region (B) and a stream ($C_4H_6$) comprising the hydrocarbons from the $C_4$ fraction which are more soluble in the selective solvent (LM) than are the butanes and the butenes is taken off from the lower combined column region (C).

Figure 1:
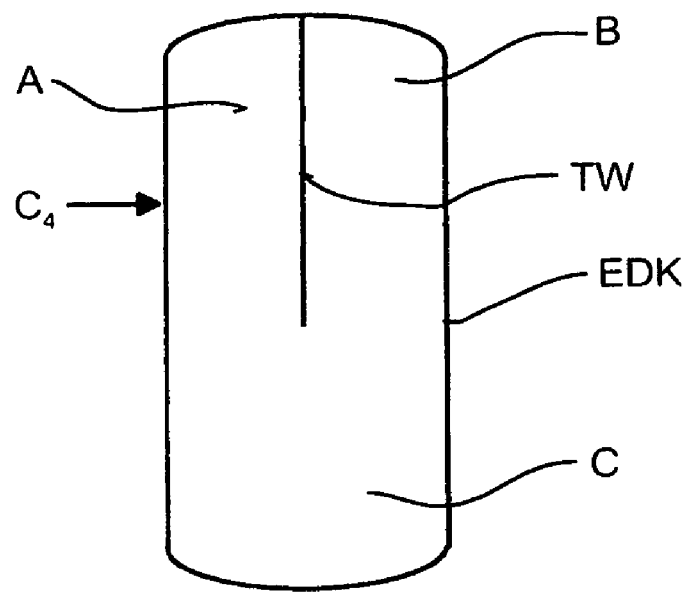

22 Claims, 2 Drawing Sheets ized by the selective solvent than are the butanes and butenes
CONTINUOUS METHOD FOR SEPARATING A C₄ CUT

CROSS REFERENCES TO RELATED APPLICATIONS

This application is a national stage application of International Patent Application No. PCT/EP03/07991 filed on Jul. 22, 2003, and claims priority to German Patent Application No. 102 33 620.2 filed on Jul. 24, 2002, both of which are incorporated herein by reference in their entireties.

The present invention relates to a continuous process for fractionating a $C_4$ fraction by extractive distillation using a selective solvent and to an extractive distillation column suitable for this purpose.

The term $C_4$ fraction refers to mixtures of hydrocarbons having predominantly four carbon atoms per molecule. $C_4$ fractions are obtained, for example, in the production of ethylene and/or propylene by thermal cracking, usually in steam crackers or FCC (Fluid Catalytic Cracking) plants, of a petroleum fraction such as liquefied petroleum gas, naphtha, or gas oil. $C_4$ fractions are also obtained in the catalytic dehydrogenation of n-butane and/or n-butene. $C_4$ fractions generally comprise butanes, n-butene, isobutene, 1,3-butadiene, together with small amounts of other hydrocarbons including butynes, in particular 1-butyne (ethylacetylene) and butenyne (vinylacetylene). The 1,3-butadiene content of $C_4$ fractions from steam crackers is generally from 10-80% by weight, preferably from 20-70% by weight, in particular from 30-60% by weight, while the content of vinylacetylene and ethylacetylene generally does not exceed 5% by weight.

The fractionation of $C_4$ fractions is a complicated distillation problem because of the small differences in the relative volatilities of the components. Fractionation is therefore carried out by extractive distillation, i.e. a distillation with addition of a selective solvent (also referred to as extractant) which has a boiling point higher than that of the mixture to be fractionated and increases the differences in the relative volatilities of the components to be separated.

Many processes are known for the fractionation of $C_4$ fractions by means of extractive distillation using selective solvents. In all of them, the gaseous $C_4$ fraction to be fractionated is brought into countercurrent contact with the liquid selective solvent under appropriate thermodynamic conditions, generally at low temperatures, frequently in the range of 20-80° C., and at moderate pressures, frequently from atmospheric pressure to 6 bar, so that the selective solvent is loaded with the components of the $C_4$ fraction for which it has a relatively high affinity, while the components for which the selective solvent has a lower affinity remain in the vapor phase and are taken off at the top. The components are subsequently fractionally liberated from the laden solvent stream in one or more further process steps under suitable thermodynamic conditions, i.e. at higher temperature and/or lower pressure compared to the first process step.

The extractive distillation of $C_4$ fractions is frequently carried out in such a way that the components of the $C_4$ fraction for which the selective solvent has a lower affinity than for 1,3-butadiene, in particular the butanes and the butenes, remain essentially in the gas phase while 1,3-butadiene and further hydrocarbons for which the selective solvent has a higher affinity than for 1,3-butadiene are essentially completely absorbed by the selective solvent. The gas phase is taken off at the top and is frequently referred to as raffinate 1. Such a process is described, for example, in DE-A 198 188 10, where the raffinate 1 is the stream denoted by Gbc taken off from the top of the extractive distillation column E I in FIGS. 1 and 2.

However, for the further use of raffinate 1, it is generally more economical for the butanes and butenes to be present as separate streams. The apparatuses used in the subsequent steps for the further processing of the butenes can be made smaller as a result and the butanes can be obtained directly as valuable cracker feed.

DE-A 102 193 75 therefore proposes a process for fractionating a $C_4$ fraction by extractive distillation so as to give butanes and butenes in separate streams. However, this requires two process stages, with a butane-containing top stream being taken off from a scrubbing zone in a first process stage I and a butene-containing top stream being taken off from a degassing zone in a second process stage II.

It is an object of the invention to provide an improved, in particular more economical and less energy-intensive, process for separating a $C_4$ fraction into 1,3-butadiene, butenes and butanes as three separate streams by extractive distillation and to provide an extractive distillation column suitable for this purpose. We have found that this object is achieved by a continuous process for fractionating a $C_4$ fraction by extractive distillation using a selective solvent in an extractive distillation column, wherein a dividing wall is installed in the longitudinal direction in the extractive distillation column to form a first region, a second region and a lower combined column region and a top stream comprising the butanes is taken off from the first region, a top stream comprising the butenes is taken off from the second region and a stream comprising the hydrocarbons from the $C_4$ fraction which are more soluble in the selective solvent than are the butanes and the butenes is taken off from the lower combined column region.

The present invention thus provides a process for fractionating a $C_4$ fraction by extractive distillation and also a suitable extractive distillation column which make it possible for butanes and butenes to be separated off as separate streams from the top of a single extractive distillation column.

According to the present invention, the extractive distillation is carried out in a dividing wall column in which a dividing wall is installed so as to form a first region, a second region and a lower combined column region.

Dividing wall columns are, as is known, used for relatively complex separation tasks, generally for mixtures of at least three components which are each to be obtained in pure form. They have a dividing wall, i.e. a flat sheet which is generally aligned in the longitudinal direction of the column and prevents crossmixing of liquid and vapor streams in the regions of the column.

For the present purposes, use is made of a particular type of dividing wall column whose dividing wall continues through to the uppermost point of the column and thus allows mixing of liquid and vapor streams only in the lower combined column region. The regions referred to as the first and second regions are separated from one another by the dividing wall.

The length of the dividing wall and also its horizontal position in the extractive distillation column can be different depending on the composition of the $C_4$ fraction fed to the extractive distillation column and on the specifications for the fractions to be separated off by means of the extractive distillation column. It is thus possible, for example, for the dividing wall to be located centrally or away from the center.

According to the present invention, a top stream comprising the butanes is taken off from the first region of the extractive distillation column configured as a dividing wall column and a top stream comprising the butenes is taken off from the second region. A stream *comprising the hydrocarbons from the $C_4$ fraction which are more soluble in the selective solvent than are the butanes and the butenes is taken off from the lower combined column region.

The solvents which are suitable for the present separation task are ones whose affinity for hydrocarbons increases from hydrocarbons having single bonds to hydrocarbons having double bonds and further to hydrocarbons having conjugated double bonds and triple bonds, preferably dipolar, particularly preferably dipolar aprotic, solvents. To protect the apparatus, substances which are noncorrosive or have a low corrosivity are preferred.

Examples of suitable selective solvents for the process of the present invention are butyrolactone, nitriles such as acetonitrile, propionitrile, methoxypropionitrile, ketones such as acetone, furfural, N-alkyl-substituted lower aliphatic acid amides, such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone, hereinafter referred to as NMP for short. Use is generally made of alkyl-substituted lower aliphatic acid amides or N-alkyl-substituted cyclic acid amides. Dimethylformamide, acetonitrile, furfural and in particular NMP are particularly advantageous.

However, it is also possible to use mixtures of these solvents among one another, for example a mixture of NMP with acetonitrile, or mixtures of these solvents with cosolvents such as water and/or tert-butyl ethers, for example methyl tert-butyl ether, ethyl tert-butyl ether, propyl tert-butyl ether, n- or iso-butyl tert-butyl ether.

A particularly useful solvent is NMP, preferably in aqueous solution, advantageously containing from 0-20% by weight of water, in particular from 7-10% by weight of water, particularly preferably 8.3% by weight of water.

As $C_4$ fraction for use in the present process, it can be advantageous to use a mixture of hydrocarbons obtained by thermal cracking of a petroleum fraction. Such a mixture typically has compositions in % by weight in the following ranges:

| | |
|---|---|
| 1,3-butadiene | from 10 to 80 |
| butenes | from 10 to 60 |
| butanes | from 5 to 40 |
| other $C_4$-hydrocarbons | from 0.1 to 5 |
| and other hydrocarbons, in particular $C_3$- and $C_5$-hydrocarbons | from 0 to not more than 5. |

However, the invention is not restricted in respect of the $C_4$ fractions which can be used. For example, it is also possible to use $C_4$ fractions from FCC (Fluid Catalytic Cracking) plants, which generally comprise from 20-70% by weight of butanes, from 30-80% by weight of butenes and other $C_3$-$C_5$-hydrocarbons as balance.

The $C_4$ fraction is fed in gaseous or liquid form into the extractive distillation column, preferably into the first region which is partitioned off by means of the dividing wall. The $C_4$ fraction is particularly preferably fed in at about the middle of the first region of the extractive distillation column.

The selective solvent is introduced as a liquid stream into both regions of the extractive distillation column, in each case in the upper part of the region.

Preference is given to taking off a stream comprising the butanes in vapor form as top stream from the first region of the extractive distillation column, condensing it in a condenser at the top of the column, returning part of the condensate as runback to the first region and taking off the remainder.

Correspondingly, a top stream comprising the butenes is taken off from the second region of the extractive distillation column and is preferably condensed in a condenser, part of the condensate is returned as runback to the second region and the remainder is taken off.

The form of words used above stating that the top stream from the region of the extractive distillation column in each case comprises butanes or butenes means that the respective streams comprise, depending on the required specification, predominantly butanes or butenes, i.e. generally at least 80% by weight of butanes or butenes, preferably from 95-99% by weight of butanes or butenes. In specific cases, specifications having purities of above 99% by weight of butanes or butenes may also be required. The further components of the respective top streams are, in particular, butanes in the butene stream and vice versa and also traces of further hydrocarbons.

According to the present invention, a stream comprising the hydrocarbons from the $C_4$ fraction which are more soluble in the selective solvent than are the butanes and the butenes is taken off from the lower combined column region of the extractive distillation column.

Preference is given to taking off the stream comprising the hydrocarbons from the $C_4$ fraction which are more soluble in the selective solvent than are the butanes and the butenes as side stream from the lower combined column region and taking off the selective solvent as bottom stream. In this embodiment, a desorption step for separating off the hydrocarbons from the solvent laden therewith is thus integrated into the lower part of the lower combined region of the extractive distillation column. However, it is likewise possible to carry out the desorption step in an apparatus separate from the extractive distillation column, i.e. firstly taking off the hydrocarbons from the $C_4$ fraction which are more soluble in the selective solvent than are the butanes and the butenes together with the selective solvent as bottom stream from the extractive distillation column.

A dividing wall column as extractive distillation column is equivalent to an assembly of two or more, in particular two or three, thermally coupled columns. The energy requirement here is comparable to that for the corresponding dividing wall column. The invention thus also encompasses all variants of the apparatus in which the extractive distillation column is configured not as a dividing wall column but as two or more, in particular two or three, thermally coupled columns.

The invention is not limited in terms of the separation-active internals which can be used in the extractive distillation column.

The number of theoretical plates in the region of the dividing wall is dependent, in particular, on the composition of the $C_4$ fraction fed in, on the solvent used and on the required specifications for the top stream comprising the butanes and that comprising the butenes. Preference is given to from 10-80 theoretical plates, in particular 25 theoretical plates, being located in the region of the dividing wall in the extractive distillation column.

The composition of the $C_4$ fraction fed in, the solvent used and the required specifications for the top stream comprising the butanes and that comprising the butenes are also critical factors in the selection of the feed tray for the $C_4$ fraction, preferably in the first region of the extractive distillation column, and for the inflow rates of the selective solvent introduced in the upper part of the first and second regions.

A condenser for the vapor streams is advantageously provided in each of the regions at the top of the extractive distillation column.

In addition, it is advantageous to carry out a heterogeneously catalyzed selective hydrogenation of the hydrocarbons containing triple bonds from the $C_4$ fraction to hydrocarbons containing double bonds by means of hydrogen in the extractive distillation column. This requires the installation of suitable internals provided with heterogeneous catalysts in the extractive distillation column and the introduction of a stream of hydrogen into the column, preferably below the inlet for the $C_4$ fraction, in the lower combined region of the extractive distillation column.

The stream comprising the butenes, i.e. 1-butene, 2-butenes (cis and trans) and isobutene, obtained in the present process can be processed further in various ways.

The term "comprising predominantly" used in the following description in the context of identification of streams means that the streams contain at least 60% by weight, preferably at least 80% by weight, particularly preferably at least 95% by weight, of the main component indicated in each case.

The further processing can advantageously be carried out to give isobutene as a single desired product or additionally to give a product comprising 1-butene or a product comprising 2-butenes.

In a first process variant, the further processing can be carried out in a reactive distillation column to give a stream comprising predominantly isobutene and a stream comprising predominantly 2-butenes, with the 1-butene being hydroisomerized to 2-butenes in the reactive distillation column and the stream comprising predominantly isobutene being taken off as top stream from the reactive distillation column and the stream comprising predominantly 2-butenes being taken off as bottom stream from the reactive distillation column.

In a further process variant, the stream comprising the butenes is subjected to a selective etherification of the isobutene and separation into a stream comprising the isobutene ether and a stream comprising 1-butene and 2-butenes, and the stream comprising 1-butene and 2-butenes is subsequently processed further by gas-phase isomerization of the 2-butenes to give a stream comprising predominantly 1-butene or by hydroisomerization of the 1-butene to give a stream comprising predominantly 2-butenes.

It is also possible to carry out the further processing by skeletal isomerization of 1-butenes and 2-butenes to isobutenes, giving a stream comprising predominantly isobutene.

The further processing of the butenes-containing stream obtained by the present process can also be carried out so as to give no isobutene as desired product, but instead be carried out according to one of the following process variants:

In one process variant, isobutene is separated off and worked up by skeletal isomerization to give a stream comprising predominantly 1-butene and 2-butenes.

In a further variant, isobutene is separated off and processed further by hydrogenation to give a stream comprising predominantly isobutane which is preferably fed to a cracker or is processed further by skeletal isomerization to give a stream comprising predominantly n-butane and dehydrogenation of the latter to give a stream comprising predominantly 1-butene and 2-butenes.

It is also possible for the isobutene in the stream comprising the butenes to be selectively dimerized to the corresponding $C_8$ hydrocarbons. The $C_8$ hydrocarbons can subsequently be separated off from a stream comprising 1-butene and 2-butenes in a simple distillation.

In a preferred process variant, the stream comprising the hydrocarbons which are more soluble in the selective solvent than are the butanes and the butenes which is taken off from the extractive distillation column is worked up further by distillation. Here, the stream comprising the hydrocarbons which are more soluble in the selective solvent than are the butanes and butenes which is taken off from the extractive distillation column is fed to a first distillation column in which it is separated into a top stream comprising 1,3-butadiene, propyne, possibly further low boilers and possibly water, and a bottom stream comprising 1,3-butadiene, 1,2-butadiene, acetylenes and possibly further high boilers, with the proportion of 1,3-butadiene in the bottom stream from the distillation column being regulated so that it is sufficiently high to dilute the acetylenes to outside the range in which there is a risk of spontaneous decomposition. The top stream from the first distillation column is fed to a second distillation column and in this is separated into a top stream comprising propyne, possibly further low boilers and possibly water and a bottom stream comprising pure 1,3-butadiene.

The stream fed to the work-up by distillation comprises predominantly 1,3-butadiene and is therefore referred to as crude 1,3-butadiene stream.

The composition of the crude 1,3-butadiene stream depends on the composition of the $C_4$ fraction which was fed to the extractive distillation and generally comprises all the acetylenes, all the 1,2-butadiene, from 30-70% of the cis-2-butene and at least 99% of the 1,3-butadiene from the $C_4$ fraction.

For the present purposes, the hydrocarbons which have boiling points lower than that of 1,3-butadiene are referred to as low boilers and the hydrocarbons which have boiling points higher than that of 1,3-butadiene are referred to as high boilers. A typical low boiler is propyne, and high boilers are predominantly hydrocarbons having a triple bond, hereinafter referred to as acetylenes, in particular 1-butyne (ethylacetylene) and butenyne (vinylacetylene).

The term "possibly" used in the present description in the context of the composition of streams obtained in the work-up by distillation means that the components qualified in this way may be present in the respective streams depending on the specific process conditions, in particular depending on the composition of the $C_4$ fraction used, the solvent used and/or auxiliaries used.

The separation of the acetylenes and 1,2-butadiene from the crude 1,3-butadiene by distillation is a complicated distillation problem because of their high reactivity and the small differences in the relative volatilities of the components making up the crude 1,3-butadiene stream. However, it has surprisingly been found that the acetylenes and 1,2-butadiene can be separated off by distillation with a justifiable energy consumption and at the same time a safe process can be ensured when the acetylenes and 1,2-butadiene are taken off as bottom stream from a distillation column and are thus diluted with 1,3-butadiene to outside the range in which there is a risk of spontaneous decomposition. For this purpose, dilution of the bottom stream to below 30 mol % of acetylenes is generally sufficient.

In a preferred process variant, the crude 1,3-butadiene stream taken off from the extractive distillation column or a downstream desorption column is therefore subjected, in a distillation column, to fractional distillation which does not produce a sharp separation in respect of 1,3-butadiene. Here, the acetylenes are taken off as a bottom stream which is diluted with 1,3-butadiene to outside the range in which there is a risk of spontaneous decomposition. Otherwise, butadiene together with propyne and possibly further low boilers is taken off from the top of the distillation column.

The top stream from the distillation column is preferably condensed in a condenser at the top of the column, part of the condensate is returned as runback to the column and the remainder is passed to a second distillation column in which it is separated into a top stream comprising propyne and possibly further low boilers and a bottom stream comprising pure 1,3-butadiene.

In both of the above-described distillation columns, it is in principle possible to use all separation-active internals customary for butadiene distillation. Owing to their lower fouling tendency, trays are particularly useful.

For the present purposes, the term pure 1,3-butadiene refers to a stream having a 1,3-butadiene content of at least 99% by weight, preferably at least 99.6% by weight, with the balance being impurities, in particular 1,2-butadiene and cis-2-butene.

In a preferred process variant, the bottom stream from the first distillation column and the top stream from the second distillation column are passed to a reactive distillation column in which a heterogeneously catalyzed selective hydrogenation of the hydrocarbons containing triple bonds to hydrocarbons containing double bonds is carried out by means of hydrogen to give a top stream comprising 1,3-butadiene, butenes, butenes and residual non-hydrogenated hydrocarbons having triple bonds and a bottom stream comprising high boilers which is discharged.

In particular, vinylacetylene is selectively hydrogenated to the useful product 1,3-butadiene.

The top stream from the reactive distillation column is preferably recycled to the extractive distillation column. However, it is also possible to take the stream from the top of the reactive distillation column or a substream thereof from the plant and process it further, for example in a cracker, or burn it.

The preferred process variant with selective hydrogenation of the acetylenes downstream of the extractive distillation is advantageous from a process engineering point of view, in particular in respect of the possible choices of catalyst, since the selective hydrogenation is carried out in a process step in which virtually no selective solvent remains in the reaction mixture. If, on the other hand, the selective hydrogenation were to be carried out, as in known processes, in the extractive distillation column and thus in the presence of the selective solvent, the choice of catalyst would be restricted considerably by the selective solvent which can make the hydrogenation less selective. In contrast, the selective hydrogenation downstream of the extractive distillation is subject to no such restrictions in terms of the choice of catalyst.

The present invention also provides an extractive distillation column for fractionating a $C_4$ fraction by extractive distillation using a selective solvent, wherein a dividing wall is installed in the longitudinal direction in the extractive distillation column to form a first region, a second region and a lower combined column region, with a top stream comprising the butanes being taken off from the first region, a top stream comprising the butenes being taken off from the second region and a stream comprising the hydrocarbons from the $C_4$ fraction which are more soluble in the selective solvent than are the butanes and the butenes being taken off from the lower combined column region.

The invention is illustrated below with the aid of a drawing and examples.

Figure 2:
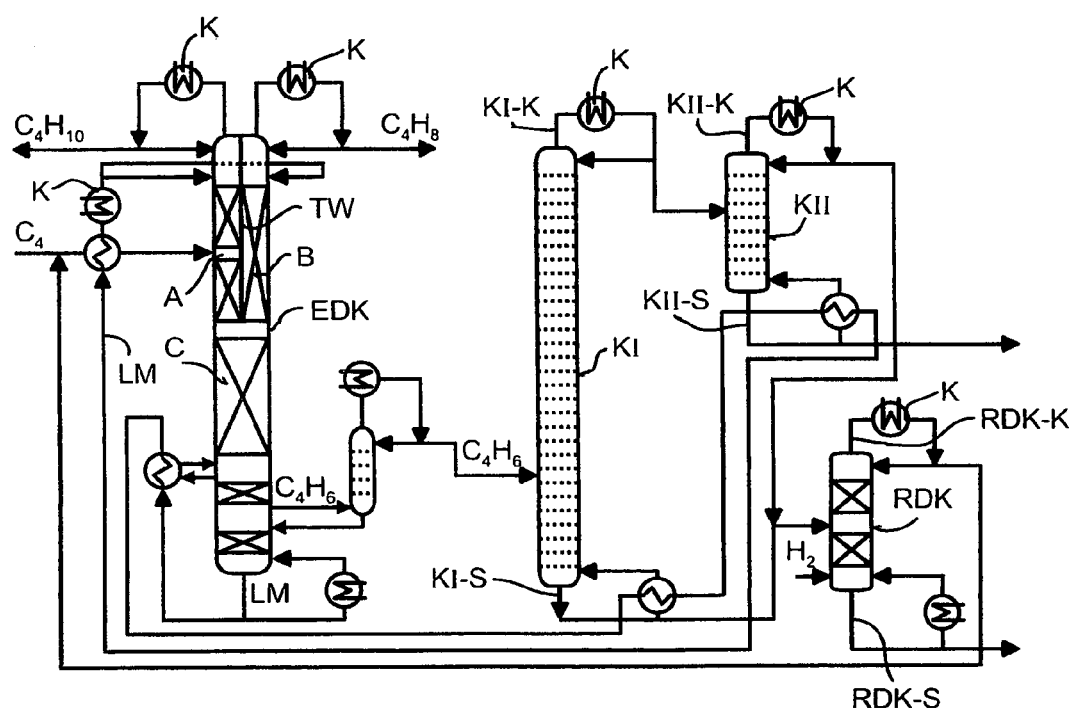

In the drawing:

FIG. 1 schematically shows an extractive distillation column EDK with dividing wall TW, and FIG. 2 schematically shows a preferred embodiment of a plant for fractionating a $C_4$ fraction in an extractive distillation column with downstream fractional distillation of the crude 1,3-butadiene stream from the extractive distillation column in two distillation columns and downstream selective hydrogenation.

The extractive distillation column EDK schematically shown in FIG. 1 has a dividing wall TW which is installed in the longitudinal direction of the column and continues through to the uppermost point of the extractive distillation column EDK and divides the column into a first region A, a second region B and a lower combined column region C. The $C_4$ fraction $C_4$ is fed into the extractive distillation column EDK in its region A.

The plant depicted schematically in FIG. 2 shows an extractive distillation column EDK for fractionating a $C_4$ fraction ($C_4$) which has a dividing wall TW which is installed in the longitudinal direction in the upper part of the column and divides the extractive distillation column EDK into a first region A, a second region B and a lower combined column region C. The $C_4$ fraction ($C_4$), which, as shown in the figure, can advantageously be heated, in particular vaporized, in a heat exchanger by heat exchange with the selective solvent LM, is fed into the extractive distillation column EDK in the first region A of the column. A liquid stream of the selective solvent LM which, as shown in the figure, is advantageously cooled by heat exchange with the $C_4$ fraction and subsequently in a condenser is introduced, in each case from the top, into each of the two regions A and B. A top stream $C_4H_{10}$ comprising the butanes is taken off from the first region A of the extractive distillation column EDK, condensed in a condenser K, part of the condensate is returned as runback to the first region A of the extractive distillation column EDK and the remainder is taken off. Analagously, a top stream $C_4H_8$ comprising the butenes is taken off from the second region B of the extractive distillation column EDK, condensed in a condenser K, part of the condensate is returned as runback to the second region B and the remainder is taken off.

A stream $C_4H_6$ comprising the hydrocarbons which are more soluble in the selective solvent than are the butanes and the butenes, predominantly 1,3-butadiene, is taken off from the lower combined column region C of the extractive distillation column EDK.

The stream $C_4H_6$ is preferably fed, as shown in FIG. 2, to a short side column S in which the stream $C_4H_6$ is distilled and a bottom stream comprising the solvent is taken off and returned to the extractive distillation column EDK. The short side column, whose use is not absolutely necessary, thus serves to recover traces of solvent from the crude 1,3-butadiene stream.

A stream comprising predominantly the selective solvent LM is taken off from the bottom of the extractive distillation column EDK. The heat in the solvent is, depending on specific conditions related to the site where the plant is located, in particular availability of coolants, integration into other plants or further processing chains, removed via various heat exchangers and the cooled solvent stream is finally recycled to the extractive distillation column EDK, in the upper region thereof.

The side stream from the extractive distillation column EDK, namely the stream $C_4H_6$, for the present purposes referred to as crude 1,3-butadiene stream, is fed to a first distillation column K I where it is separated into a top stream K I-K and a bottom stream K I-S. The top stream K I-K is condensed in a condenser K at the top of the column, part of the condensate is returned as runback to the column and the remainder is taken off and passed to a second distillation column K II. The bottom stream K I-S is taken off and fed to a reactive distillation column RDK.

In the second distillation column K II, the condensate from the first distillation column is fractionated to give a top stream K II-K which is condensed in a condenser K, part of the condensate is returned as runback to the column and the remainder is likewise passed to the reactive distillation column RDK. The bottom stream K II-S from the second distillation column K II is taken off as pure 1,3-butadiene stream.

In the reactive distillation column RDK, the hydrocarbons containing triple bonds are selectively hydrogenated to hydrocarbons containing double bonds by means of hydrogen in the presence of a heterogeneous catalyst. A top stream RDK-K is taken off, condensed in a condenser K, part of the condensate is returned to the reactive distillation column RKD and the remainder is preferably, as shown in the figure, recycled to the extractive distillation column EDK.

The bottom stream from the reactive distillation column, namely stream RDK-S, which comprises predominantly high boilers, is discharged from the plant and is preferably burnt.

EXAMPLE

Extractive Distillation

A $C_4$ fraction from a steam cracker having the composition reported below in % by weight was fed to an extractive distillation column which was configured as a dividing wall column having a dividing wall going through to the uppermost point of the column and had a total of 80 theoretical plates of which 25 were in the region of the dividing wall. The $C_4$ fraction was introduced into the first region denoted in the drawing by A on the 68th theoretical plate, counting from the bottom. NMP containing 8.3% by weight of water was used as selective solvent.

| | |
|---|---|
| Propene | 0.02 |
| propadiene | 0.04 |
| propyne | 0.06 |
| n-butane | 5.74 |
| i-butane | 2.44 |
| n-butene | 13.88 |
| i-butene | 25.63 |
| t-2-butene | 4.44 |
| cis-2-butene | 2.95 |
| 1,3-butadiene | 43.81 |
| 1,2-butadiene | 0.14 |
| 1-butyne | 0.12 |
| vinylacetylene | 0.73 |

A top stream comprising predominantly butanes was taken off from the first region A of the extractive distillation column EDK; this had the following composition in % by weight:

| | |
|---|---|
| Propene | 0.19 |
| n-butane | 62.02 |
| i-butane | 27.98 |
| n-butene | 6.63 |
| i-butene | 2.71 |
| trans-2-butene | 0.24 |
| $H_2O$ | 0.23 |

A top stream comprising predominantly butenes was taken off from the region B of the extractive distillation column; this had the following composition in % by weight:

| | |
|---|---|
| Propadiene | 0.07 |
| n-butane | 0.91 |
| i-butane | 0.10 |
| n-butene | 28.57 |
| i-butene | 54.55 |
| trans-2-butene | 9.48 |
| cis-2-butene | 6.32 |

Compared to a known process in which butanes and butenes are separated off together in an extractive distillation column and are subsequently separated in an additional apparatus, an energy saving of about 20% was achieved.

EXAMPLE

Work-Up of Crude 1,3-butadiene by Distillation

A crude 1,3-butadiene stream obtained by extractive distillation as described in the above example from the $C_4$ fraction described there was fed to a distillation column having 80 theoretical plates on the 25th plate, counted from the bottom. The crude 1,3-butadiene stream $C_4H_6$ had the following composition in % by weight:

| | |
|---|---|
| Propyne | 0.11 |
| 1,3-butadiene | 98.58 |
| 1,2-butadiene | 0.30 |
| 1-butyne | 0.30 |
| vinylacetylene | 0.56 |
| water | 0.15 |

In the distillation column K I, this stream $C_4H_6$ was separated into a top stream K I-K having the following composition in % by weight:

| | |
|---|---|
| Propyne | 0.11 |
| 1,3-butadiene | 99.73 |
| water | 0.16 | and a bottom stream K I-S having the following composition in % by weight:

| | |
|---|---|
| cis-2-butene | 0.52 |
| 1,3-butadiene | 40.0 |
| 1,2-butadiene | 15.1 |
| 1-butyne | 13.75 |
| vinylacetylene | 29.17 |
| 3-methyl-1-butene | 0.98 |
| 2-methyl-2-butene | 0.48 |

The top stream K I-K from the first distillation column K I was divided into an offtake stream (1/7 of the top stream K I-K) and a runback stream (6/7 of the top stream k I-K). The offtake stream was fed into a second distillation column K II having 25 theoretical plates on the 14th theoretical plate and fractionated to give a top stream K II-K having the following composition in % by weight:

| | |
|---|---|
| Propyne | 79.52 |
| 1,3-butadiene | 20.0 and |
| water | 0.48 | and a bottom stream K II-S comprising pure 1,3-butadiene and having a 1,3-butadiene content of 99.99%. The bottom stream K II-S was taken off as desired product.

The energy which had to be supplied from the outside in the above-described fractionation according to the present invention of a $C_4$ fraction in an extractive distillation column to give a stream comprising the butanes, a stream comprising the butenes and a stream comprising crude 1,3-butadiene with subsequent work-up of the crude 1,3-butadiene stream by distillation was 15% lower than in the case of a known process in which butanes and butenes are separated off in separate process stages, as described, for example, in the German patent application 102 19 375, and the acetylenes are separated off from the crude 1,3-butadiene stream by extractive distillation using a selective solvent, as described, for example, in the German patent application 101 05 660.

We claim:

1. A continuous process for fractionating a $C_4$ fraction by extractive distillation using a selective solvent in an extractive distillation column having a dividing wall that extends in the longitudinal direction to an uppermost point of the extractive distillation column to form a first region, a second region and a lower combined column region, wherein the process comprises:
    taking off from the first region a top stream comprising predominantly one or more butanes;
    taking off from the second region a top stream comprising predominantly one or more butenes; and
    taking off from the lower combined column region a stream comprising one or more hydrocarbons from the $C_4$ fraction which are more soluble in the selective solvent than are the butanes and the butenes.

2. The process according to claim 1, wherein the stream comprising the hydrocarbons from the $C_4$ fraction which are more soluble in the selective solvent than are the butanes and the butenes is taken off as a side stream from the lower combined column region and the selective solvent is taken off as a bottom stream from the extractive distillation column.

3. The process according to claim 1, wherein the stream comprising the hydrocarbons from the $C_4$ fraction which are more soluble in the selective solvent than are the butanes and the butenes is taken off together with the selective solvent as a bottom stream from the extractive distillation column.

4. The process according to claim 1, wherein the $C_4$ fraction is fed into the first region of the extractive distillation column, the top stream comprising the butanes is taken off from the first region of the extractive distillation column and the top stream comprising the butenes is taken off from the second region of the extractive distillation column.

5. The process according to claim 1, wherein two or more, thermally coupled columns are used in place of the extractive distillation column with dividing wall.

6. The process according to claim 1, wherein the selective solvent comprises one or more substances selected from the group consisting of dimethylformamide, acetonitrile, furfural, and N-methylpyrrolidone.

7. The process according to claim 1, wherein 10-80 theoretical plates are located in the region of the dividing wall of the extractive distillation column.

8. The process according to claim 1, wherein a heterogeneously catalyzed selective hydrogenation of the hydrocarbons comprising triple bonds from the $C_4$ fraction to hydrocarbons comprising double bonds is additionally carried out in the extractive distillation column.

9. The process according to claim 1, wherein the stream comprising the hydrocarbons which are more soluble in the selective solvent than are the butanes and butenes which is taken off from the extractive distillation column is fed to a first distillation column in which it is separated into a top stream comprising 1,3-butadiene, propyne, possibly further low boilers and possibly water, and a bottom stream comprising 1,3-butadiene, 1,2-butadiene, acetylenes and possibly further high boilers, with the proportion of 1,3-butadiene in the bottom stream from the distillation column being regulated so that it is sufficiently high to dilute the acetylenes to outside the range in which there is a risk of spontaneous decomposition and the top stream from the first distillation column is fed to a second distillation column and in this is separated into a top stream comprising propyne, possibly further low boilers and possibly water and a bottom stream comprising pure 1,3-butadiene.

10. The process according to claim 9, wherein the bottom stream from the first distillation column and the top stream from the second distillation column are passed to a reactive distillation column in which a heterogeneously catalyzed selective hydrogenation of the hydrocarbons comprising triple bonds to hydrocarbons comprising double bonds is carried out by means of hydrogen, with a partial conversion of the acetylenes, to give a top stream comprising 1,3-butadiene, butanes, butenes and non-hydrogenated hydrocarbons having triple bonds and a bottom stream comprising high boilers which is discharged.

11. The process according to claim 1, further comprising processing the stream comprising the butenes, isobutene, 1-butenes and 2-butenes in a reactive distillation column to give a stream comprising predominantly isobutene and a stream comprising predominantly 2-butenes, with 1-butene being hydroisomerized to 2-butenes in the reactive distillation column and the stream comprising predominantly isobutene being taken off as a top stream from the reactive distillation column and the stream comprising predominantly 2-butenes being taken off as a bottom stream from the reactive distillation column.

12. The process according to claim 1, further comprising subjecting the stream comprising the butenes to a selective etherification of the isobutene and fractionation to give a stream comprising the isobutene ether and a stream comprising 1-butene and 2-butenes and subsequently further processing the stream comprising 1-butene and the 2-butenes by gas-phase isomerization of the 2-butenes to give a stream comprising predominantly 1-butene or by hydroisomerization of the 1-butene to give a stream comprising predominantly 2-butenes.

13. The process according to claim 1, further comprising processing the stream comprising the butenes, isobutene, 1-butene and 2-butenes, by skeletal isomerization of 1-butene and 2-butenes to isobutene, to give a stream comprising predominantly isobutene.

14. The process according to claim 1, further comprising processing the stream comprising the butenes, isobutene, 1-butene and 2-butenes, by separating off isobutene and working it up by skeletal isomerization to give a stream comprising predominantly 1-butene and 2-butenes.

15. The process according to claim 1, further comprising processing the stream comprising the butenes, isobutene, 1-butene and 2-butenes, by separating off isobutene and processing it further by hydrogenation to give a stream which comprises predominantly isobutane and is preferably fed to a cracker or by skeletal isomerization to give a stream comprising predominantly n-butane and dehydrogenation of the latter to give a stream comprising predominantly 1-butene and 2-butenes.

16. The process according to claim 1, further comprising processing the stream comprising the butenes, isobutene, 1-butene and 2-butenes, by selective dimerization of isobutene to the corresponding $C_8$-hydrocarbons and subsequent fractional distillation to give a stream comprising 1-butene and 2-butenes and a stream comprising the $C_8$-hydrocarbons.

17. The process according to claim 5, wherein two or three, thermally coupled columns are used in place of the extractive distillation column with dividing wall.

18. The process according to claim 6, wherein the selective solvent is N-methylpyrrolidone in an aqueous solution.

19. The process according to claim 7, wherein 25 theoretical plates are located in the region of the dividing wall of the extractive distillation column.

20. The process according to claim 1, wherein the content of the one or more butanes in the top stream comprising predominantly one or more butanes is at least 60 wt. %, and the content of the one or more butenes in the top stream comprising predominantly one or more butenes is at least 60 wt. %.

21. The process according to claim 1, wherein the content of the one or more butanes in the top stream comprising predominantly one or more butanes is at least 80 wt. %, and the content of the one or more butenes in the top stream comprising predominantly one or more butenes is at least 80 wt. %.

22. The process according to claim 1, wherein the content of the one or more butanes in the top stream comprising predominantly one or more butanes is at least 95 wt. %, and the content of the one or more butenes in the top stream comprising predominantly one or more butenes is at least 95 wt. %.

* * * * *